(12) United States Patent
Nadim

(10) Patent No.: US 10,368,858 B1
(45) Date of Patent: Aug. 6, 2019

(54) SUTURE PASSER

(71) Applicant: Ring Orthopedics, Inc., Tampa, FL (US)

(72) Inventor: Yasser Nadim, Somerset, KY (US)

(73) Assignee: Ring Orthopedics, Inc., Tampa, FL (US)

( * ) Notice: Subject to any disclaimer, the term of this patent is extended or adjusted under 35 U.S.C. 154(b) by 0 days.

(21) Appl. No.: 16/167,761

(22) Filed: Oct. 23, 2018

Related U.S. Application Data

(60) Provisional application No. 62/622,057, filed on Jan. 25, 2018.

(51) Int. Cl.
  *A61B 17/04* (2006.01)
  *A61B 17/06* (2006.01)
(52) U.S. Cl.
  CPC ...... *A61B 17/0485* (2013.01); *A61B 17/0469* (2013.01); *A61B 17/0482* (2013.01); *A61B 17/06066* (2013.01); *A61B 2017/06052* (2013.01)
(58) Field of Classification Search
  CPC ............ A61B 17/0469; A61B 17/0482; A61B 17/0483; A61B 17/0485; A61B 17/06061; A61B 17/06066; A61B 17/06109; A61B 17/062; A61B 2017/06009; A61B 2017/06042; A61M 25/007
  See application file for complete search history.

(56) References Cited

U.S. PATENT DOCUMENTS

| | | | | |
|---|---|---|---|---|
| 5,817,112 A | * | 10/1998 | Christoudias | A61B 17/0469 606/148 |
| 8,709,022 B2 | | 4/2014 | Stone | |
| 2013/0218173 A1 | * | 8/2013 | Weisel | A61B 17/0469 606/144 |
| 2015/0282806 A1 | | 10/2015 | Jorgensen | |

* cited by examiner

*Primary Examiner* — Robert A Lynch
(74) *Attorney, Agent, or Firm* — Larson & Larson, P.A.; Justin P. Miller; Frank Liebenow

(57) ABSTRACT

The suture passer includes a body from which two mechanisms protrude: a hollow needle through which a suture is guided, the suture exiting at the surgical site; and a sliding hollowing tube with a distal opening, exposing a resilient member. When gripping of a suture is required, the resilient member is intentionally over-extended, causing the resilient member to bow and protrude from the distal opening. A suture is then passed into the resulting gap between the sliding hollowing tube and resilient member, the resilient member then allowed to retract back into place, thereby clamping the suture.

15 Claims, 4 Drawing Sheets

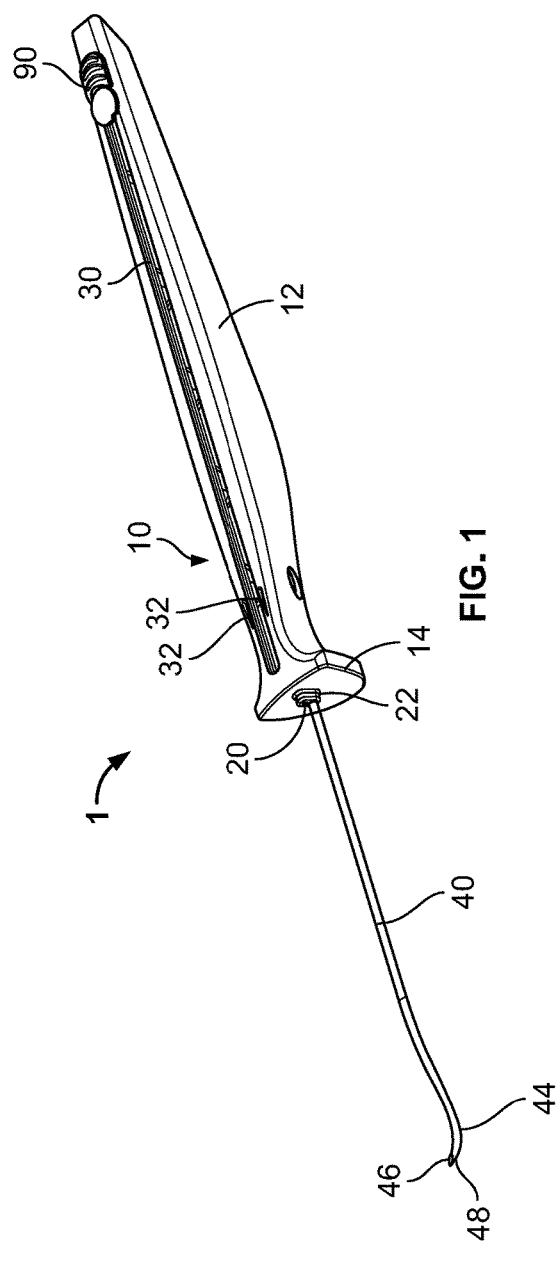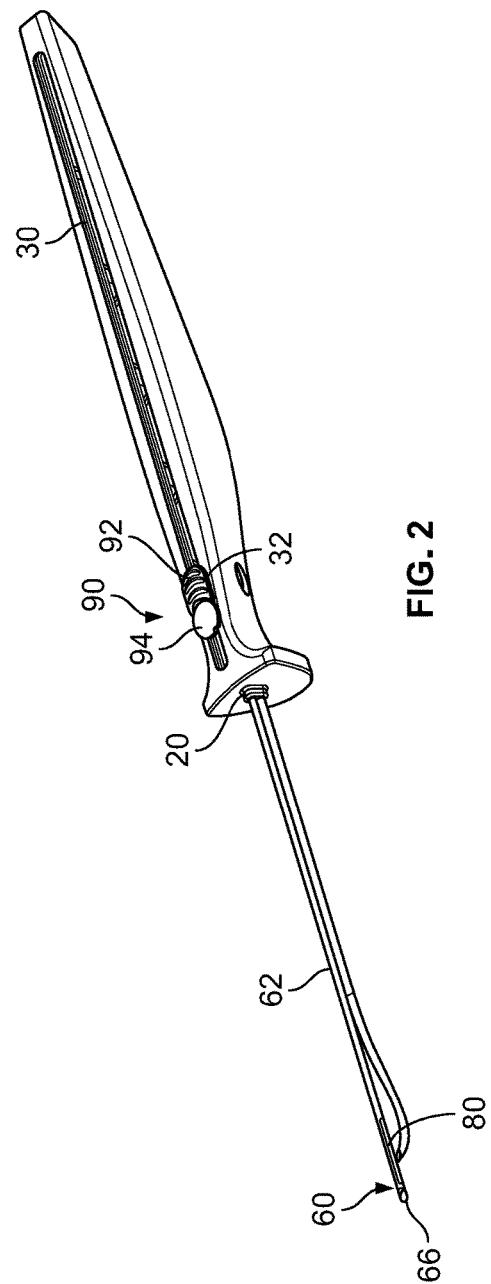

SUTURE PASSER

CROSS-REFERENCE TO RELATED APPLICATION

This application is a continuation of U.S. Pat. App. Ser. No. 62/622,057, filed Jan. 25, 2018, titled Novel suture passing and retrieving device to pass and retrieve suture and other filamentary material in arthroscopic surgery.

FIELD

This invention relates to the field of surgical instruments and more particularly to a device for gripping sutures during arthroscopic surgery.

BACKGROUND

Arthroscopic surgery is a surgical procedure performed on a joint of the body, the instruments working through a small slit in the skin.

Patients who receive arthroscopic surgery, as compared to traditional surgery with its large incisions, experience decreased recovery time and a reduced number of complications.

But the limitations of arthroscopic surgery imposed on the surgeon, including confined access created by small incisions and decreased working volume, create issues for surgeons. For example, a surgeon's hands cannot directly reach into the surgical site to retrieve a suture or tie a knot. The result is that the complexity, from the perspective of the surgeon, is increased.

Given that conventional needle and suture thread cannot access the surgical site, an alternative is needed.

What is needed is a simple, reliable device that allows suture to be passed to the surgical site, and then manipulated in-place, for use within surgical sites with limited access.

SUMMARY

The suture passer includes a body, from which two mechanisms protrude: a hollow needle through which a suture is guided, the suture exiting at the surgical site; and a sliding hollow tube with a distal opening, exposing a resilient member.

To grip a suture, the resilient member is intentionally over-extended, which causes the resilient member to bow outward and protrude from the distal opening of the sliding hollow tube. A suture is introduced into the resulting gap between the sliding hollowing tube and resilient member, the resilient member then allowed to retract back into place, thereby clamping the suture.

The hollow needle of the suture passer is fixed with respect to the body and handle. Thus, the surgeon may manipulate the handle in order to control the hollow needle. In alternative embodiments the hollow needle has multiple fixed positions with respect to the handle to provide the surgeon with placement options.

To pass a suture to the surgical site, the suture is inserted into a first end of the hollow needle through a hole in the body or handle. The suture follows the interior of the hollow needle, exiting into the surgical site at the suture exit. Prior to the exit is preferably located a curve. The curve shifts the direction of the hollow needle, and correspondingly the suture, to point toward the clamping location of the resilient member. This curve is not required, as in alternative embodiments the sliding hollow tube of the retrieval member is curved.

The hollow needle optionally includes a cutting tip to help pass the suture material through tissue.

The retrieval member is formed from a sliding hollow tube and an internal resilient member. The resilient member is formed from a flexible material with a particular shape, generally linear. When the resilient member is deformed, it creates a force to try to return itself to its original shape.

The hollow tube and resilient member are controlled by a split actuator that slides within a slot along the handle. Inside the handle the split actuator connects to an end of the hollow tube and an end of the resilient member A proximal portion of the split actuator connects to the hollow tube, and a distal portion of the split actuator connects to the resilient member. Initially, the two portions of the split actuator move together. Then the proximal actuator contacts a stop on the handle, stopping the distal opening of the hollow tube at the ideal location to receive a suture.

Further motion of the split actuator moves only the distal portion of the actuator, thereby allowing over-extension of the resilient member, causing deformation of the resilient member, creating a gap to at the distal opening to receive a suture.

Regarding materials, the body of the suture passer is preferably plastic, but may be formed from other materials such as metal.

The hollow needle sliding hollow tube is preferably formed from surgical stainless steel, such as 316, 420, or 440 stainless steel. But other materials are acceptable.

The resilient member is preferably a wire formed from nickel titanium, also referred to as Nitinol wire. Nitinol is a metal alloy of nickel and titanium in which the two elements are present in roughly equal atomic percentages. Nitinol is readily able to return to its original shape after bending, stretching, and twisting. Nitinol displays recoverable strains that are more than an order of magnitude greater than in traditional alloys.

An example of a suitable material is a Nitinol wire with a diameter of 0.05" and a circular cross-section. Preferably spring tempered with a tensile strength of 181,000 psi.

Discussion now turns to the drawings.

BRIEF DESCRIPTION OF THE DRAWINGS

The invention can be best understood by those having ordinary skill in the art by reference to the following detailed description when considered in conjunction with the accompanying drawings in which:

FIG. 1 illustrates an isometric view of a first embodiment of the suture passer with the retrieval member fully retracted.

FIG. 2 illustrates an isometric view of a first embodiment of the suture passer with the retrieval member fully extended, and the resilient member in a closed state.

DETAILED DESCRIPTION

Figure 3:
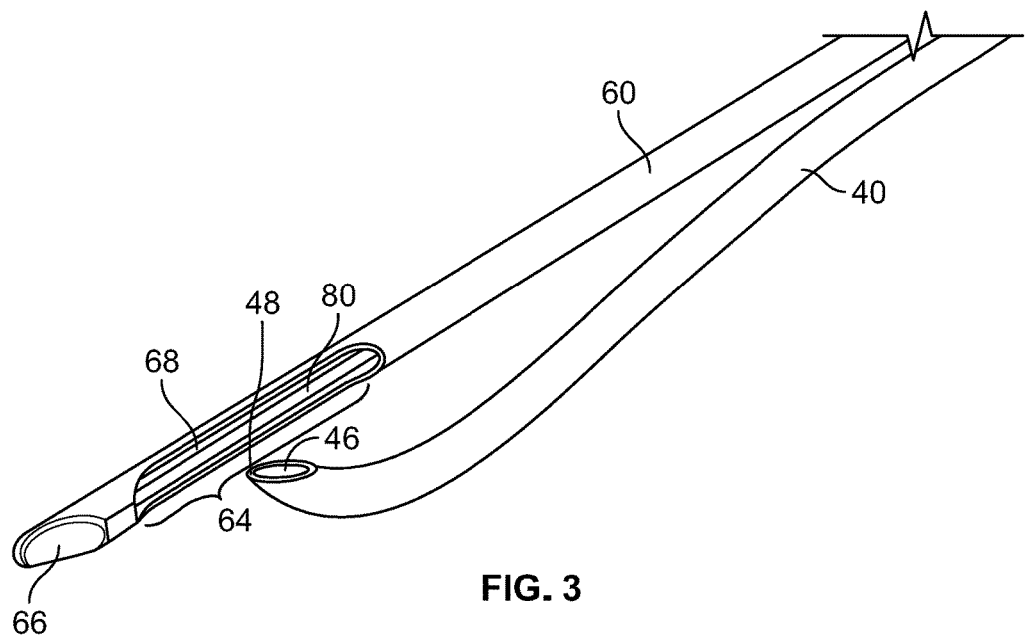
FIG. 3 illustrates a close-up of the interaction of the tip of the hollow needle and retrieval member, with the resilient member in a closed state.

Reference will now be made in detail to the presently preferred embodiments of the invention, examples of which are illustrated in the accompanying drawings. Throughout the following detailed description, the same reference numerals refer to the same elements in all figures.

Referring to FIG. 1, an isometric view is shown of a first embodiment of the suture passer 1 with the retrieval member 60 fully retracted, and thus not shown.

The suture passer 1 is formed from a body 10, which includes a grip 12 and guard 14.

Past the guard 14 are two holes that pass through the body 10—an upper hole 20 for the retrieval member and a lower hole 22 for the hollow needle.

A slot 30 at the top of the body 10 guides the movement of a split actuator 90. A stop 32 is placed along the path of the slot 30, the stop 32 interacting with the split actuator 90, as discussed further below.

The hollow needle 40 begins at a suture entrance 42, which is visible through a suture hole 16 in the body 10. The hollow needle 40 continues, passing through the lower hole 22, away from the body 10. The hollow needle changes direction at a curved guide 44 portion, terminating at the suture exit 46 with cutting tip 48.

Referring to FIG. 2, an isometric view is shown of a first embodiment of the suture passer 1 with the retrieval member 60 fully extended, and the resilient member 80 in a closed state.

The retrieval member 60 is extended through the upper hole 20, the sliding hollow tube 62 containing a resilient member 80, visible at the opening 64, also referred to as distal opening 64. The retrieval member ends in a tip 66. The resilient member 80 is optionally terminated at the tip 66, inside of the sliding hollow tube 62.

In this extended position, the proximal actuator 92 of the split actuator 90 rests against the stop 32. Any further movement of the distal actuator 94, which is not limited by the stop 32, will result in over-extension of the resilient member and a resulting protrusion of the resilient member from the opening 64.

Referring to FIG. 3, a close-up is shown of the interaction of the cutting tip 48 of the hollow needle 40 and retrieval member 60, with the resilient member 80 in a closed state.

As in FIG. 2, the split actuator 90 rests at the stop 32, and the distal actuator 94 has not yet been moved beyond that point in the slot 30. Thus, the resilient member 80 is in a resting state.

The gripping face 68, or an inner portion of the sliding hollow tube 62 exposed at the opening 64, is visible.

Figure 4:
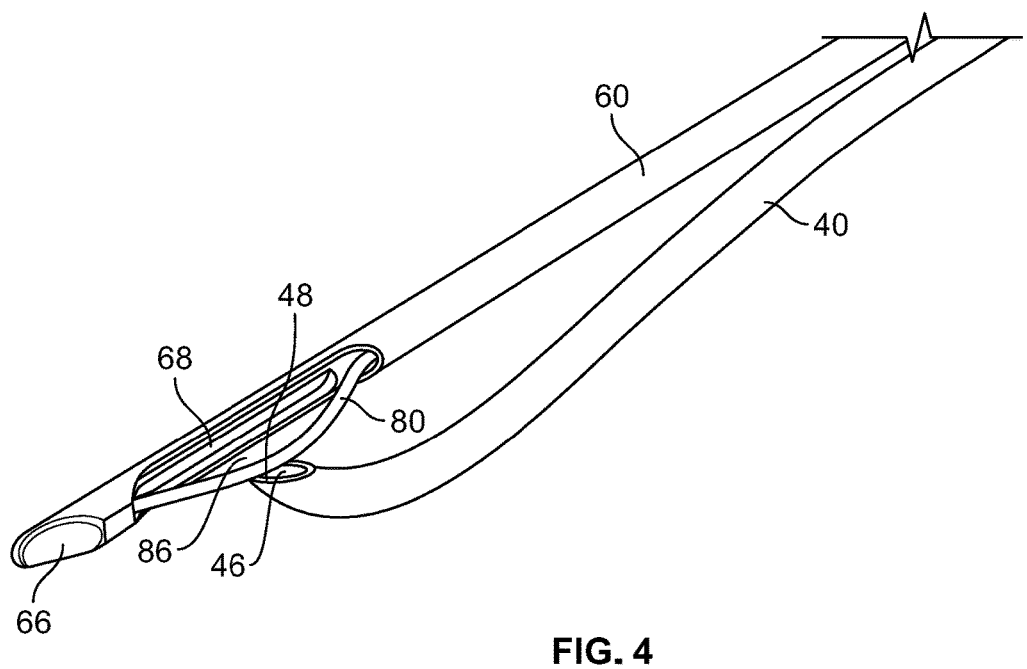
FIG. 4 illustrates a close-up of the interaction of the tip of the hollow needle and retrieval member, with the resilient member in an open state.

Referring to FIG. 4, a close-up is shown of the interaction of the cutting tip 48 of the hollow needle 40 and retrieval member 60, with the resilient member 80 in an open state.

With the resilient member 80 over-extended, the resilient member 80 protrudes through the opening 64, or distal opening 64, in the sliding hollow tube 62, creating a gap 86. The exposed portion of the inside of the sliding hollow tube 62 is the gripping face 68.

Figure 5:
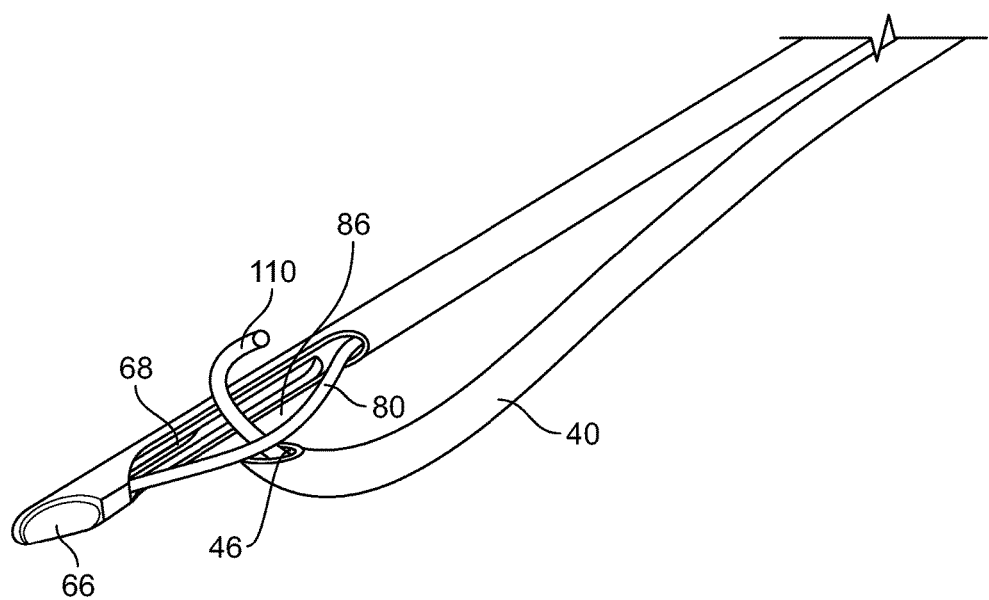
FIG. 5 illustrates a close-up of the interaction of the tip of the hollow needle and retrieval member, with the resilient member in an open state and a suture exiting the hollow needle.

Referring to FIG. 5, a close-up is shown of the interaction of the cutting tip 48 of the hollow needle 40 and retrieval member 60, with the resilient member 80 in an open state, a suture 110 exiting the hollow needle 40.

When the user releases the pressure applied to the distal actuator 94 (see FIG. 5), the gap 86 will close, gripping the suture 110 between the resilient member 80 and the gripping face 68.

Figure 6:
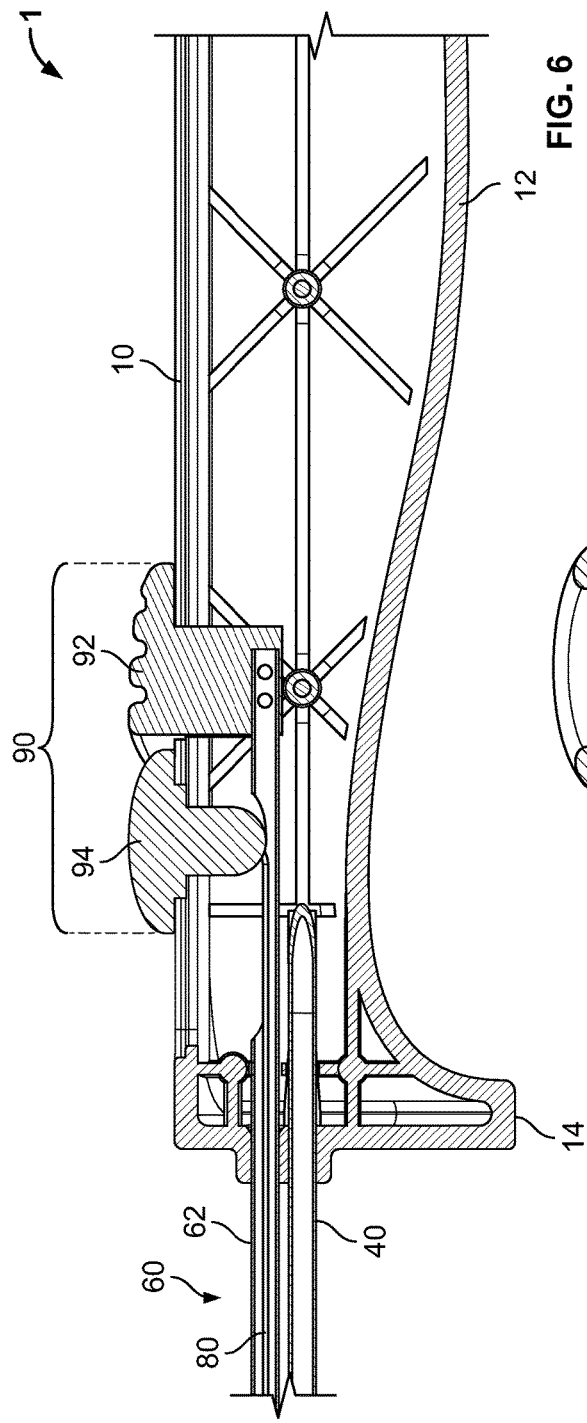
FIG. 6 illustrates a cross-section of the suture passer, showing the interaction of the split actuator and retrieval member.

Referring to FIG. 6, a cross-section of the suture passer 1 is shown, showing the interaction of the split actuator 90 and retrieval member 60.

Within the body 10, the proximal actuator 92 of the split actuator 90 interfaces with the sliding hollow tube 62. The distal actuator 94 of the split actuator 90 interfaces with the resilient member 80.

Also shown is the grip 12, guard 14, and hollow needle 40.

Figure 7:
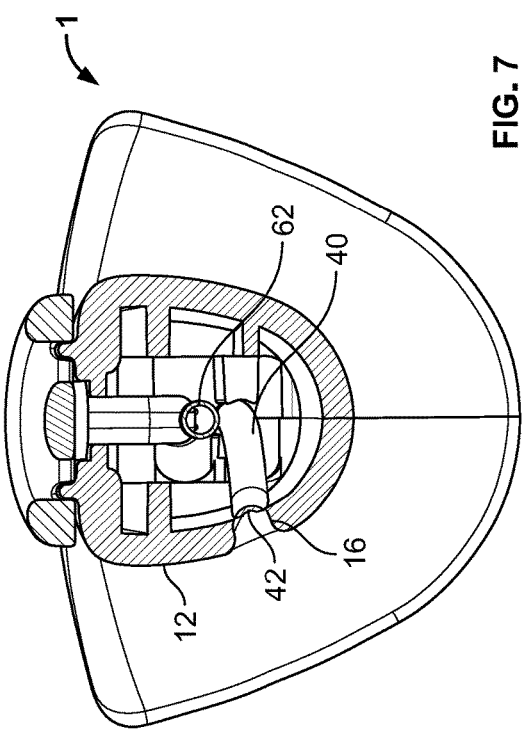
FIG. 7 illustrates a cross-section of the suture passer, showing the path of the hollow needle passing through the handle of the body of the suture passer.

Referring to FIG. 7, a cross-section is shown of the suture passer 1, showing the path of the hollow needle 40 passing through the handle 12 of the body 10 of the suture passer 1.

The hollow needle 40 curves, terminating at suture entrance 42, which coincides with a hole in the body 10, referred to as suture hole 16

Also shown is the grip 12, guard 14, and sliding hollow tube 62.

Equivalent elements can be substituted for the ones set forth above such that they perform in substantially the same manner in substantially the same way for achieving substantially the same result.

It is believed that the system and method as described and many of its attendant advantages will be understood by the foregoing description. It is also believed that it will be apparent that various changes may be made in the form, construction, and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A device to grip a suture in an enclosed space comprising:
   a hollow member with a distal opening;
   a resilient member within the hollow member;
   a handle;
   the hollow member slidably connected to the handle;
   a split actuator formed from a proximal actuator and a distal actuator, the split actuator sliding with respect to the handle:
   the proximal actuator controlling motion of the hollow member;
   the distal actuator controlling motion of the resilient member;
   whereby a force against an end of the resilient member causes the resilient member to protrude through the distal opening, creating a gap in which the suture may be grasped;
   whereby motion of the proximal actuator with respect to a body extends and retracts the hollow member; and
   whereby motion of the distal actuator with respect to the proximal actuator causes the resilient member to protrude through the distal opening.

2. The device of claim 1, further comprising: a slot in which the split actuator slides; and a stop along the slot, the stop preventing further sliding of the proximal actuator, but permitting further sliding of the distal actuator.

3. The device of claim 1, further comprising: a hollow needle, with an entrance and an exit, connected to the handle; the exit of the hollow needle near the distal opening of the hollow member when the hollow member is fully extended.

4. The device of claim 1, further comprising:
a handle;
the hollow member connected to the handle;
a hollow needle, with an entrance and an exit, connected to the handle;
the exit of the hollow needle near the distal opening of the hollow member when the hollow member is fully extended.

5. The device of claim 1, wherein the resilient member is formed from a material that prefers to maintain a first shape, and thus creates a force that oppose bending into a second shape.

6. A device that allows a user to grip a suture within a patient, the device comprising:
a handle;
a hollow tube with a distal opening and a tip;
the hollow tube connected to the handle;
a resilient member within the hollow tube;
the resilient member having a first end and a second end;
the first end of the resilient member fixed at the tip of the hollow tube;
a split actuator formed from a proximal actuator and a distal actuator, the split actuator sliding with respect to the handle:
the proximal actuator controlling motion of the hollow tube;
the distal actuator controlling motion of the resilient member:
whereby the application of pressure against the second end of the resilient member causes the resilient member to deform, protruding from the distal opening, thereby permitting an item to be gripped between the hollow tube and the resilient member;
whereby motion of the proximal actuator with respect to a body extends and retracts the hollow tube; and
whereby motion of the distal actuator with respect to the proximal actuator causes the resilient member to protrude through the distal opening.

7. The device of claim 6, further comprising: a slot in which the split actuator slides; a stop along the slot, the stop preventing further sliding of the proximal actuator, but permitting further sliding of the distal actuator.

8. The device of claim 6, further comprising: a hollow needle, with an entrance and an exit, connected to the handle; the exit of the hollow needle near the distal opening of the hollow tube when the hollow tube is fully extended.

9. The device of claim 6, further comprising:
a hollow needle, with an entrance and an exit, connected to the handle;
the exit of the hollow needle near the distal opening of the hollow tube when the hollow tube is fully extended.

10. The device of claim 6, wherein the resilient member is formed from a material that prefers to maintain a first shape, and thus creates a force that opposes bending into a second shape.

11. A device for gripping a suture within a patient, the device comprising:
a deformable resilient member held within a hollow member;
the hollow member including an opening that partially exposes the deformable resilient member;
a handle;
the hollow member slidably connected to the handle;
a split actuator formed from a proximal actuator and a distal actuator, the split actuator sliding with respect to the handle;
the proximal actuator controlling motion of the hollow member;
the distal actuator controlling motion of the deformable resilient member;
whereby when under compression, the deformable resilient member extends through the opening, creating a space for insertion of a suture, and when compression is removed, the deformable resilient member returns to its original position, able to grip a suture between the resilient member and an inner wall of the hollow member;
whereby motion of the proximal actuator with respect to a body extends and retracts the hollow member; and
whereby motion of the distal actuator with respect to the proximal actuator causes the deformable resilient member to protrude through the distal opening.

12. The device of claim 11, further comprising: a slot in which the split actuator slides; a stop along the slot, the stop preventing further sliding of the proximal actuator, but permitting further sliding of the distal actuator.

13. The device of claim 11, further comprising: a hollow needle, with an entrance and an exit, connected to the handle; the exit of the hollow needle near the distal opening of the hollow member when the hollow member is fully extended.

14. The device of claim 11, further comprising:
a handle;
the hollow member connected to the handle;
a hollow needle, with an entrance and an exit, connected to the handle;
the exit of the hollow needle near the distal opening of the hollow member when the hollow member is fully extended.

15. The device of claim 11, wherein the resilient member is formed from a material that prefers to maintain a first shape, and thus creates a force that opposes bending into a second shape.

* * * * *